United States Patent [19]

Roy et al.

[11] Patent Number: 4,654,439
[45] Date of Patent: Mar. 31, 1987

[54] L-AMINODICARBOXYLIC ACID AMIDES OF ALKOXYALKYLAMINES

[75] Inventors: Glenn M. Roy, Garnerville; Ronald E. Barnett, Suffern; Paul R. Zanno, Nanuet, all of N.Y.

[73] Assignee: General Foods Corporation, White Plains, N.Y.

[21] Appl. No.: 842,571

[22] Filed: Mar. 21, 1986

Related U.S. Application Data

[62] Division of Ser. No. 738,202, May 24, 1985, Pat. No. 4,603,011.

[51] Int. Cl.$^4$ ............... C07C 61/06; C07C 61/16; C07C 61/20; C07C 101/30
[52] U.S. Cl. .................... 562/503; 562/505; 562/564; 426/548
[58] Field of Search ............ 562/505, 503, 564

[56] References Cited

U.S. PATENT DOCUMENTS 3,798,204  3/1974  Nakajima et al. ............ 530/801
3,971,822  7/1976  Chibata et al. ............... 562/564
4,338,346  7/1982  Brand ........................... 562/564
4,423,029 12/1983  Rizzi ............................. 562/503
4,571,345  2/1986  Verlander et al. ............ 562/503

Primary Examiner—John Kight
Assistant Examiner—Nathan M. Nutter
Attorney, Agent, or Firm—Linn I. Grim; Thomas A. Marcoux; Daniel J. Donovan

[57] ABSTRACT

The present invention is directed to new sweeteners of the formula:

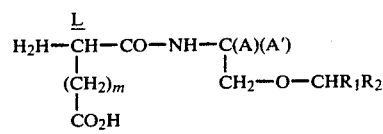

wherein,
A is H, alkyl containing 1–3 carbon atoms, hydroxyalkyl containing 1–3 carbon atoms, alkoxymethyl wherein the alkoxy group contains 1–3 carbon atoms, or $CO_2R$ in which R is alkyl containing 1–3 carbon atoms;
A' is H or $CH_3$;
A and A' when taken together with the carbon atom to which they are attached form a cycloalkyl containing 3–4 carbon atoms;
$R_1$ and $R_2$ are each a branched-chain alkyl containing 3–5 carbon atoms; and
m=0 or 1;
and food-acceptable salts thereof.

35 Claims, No Drawings

L-AMINODICARBOXYLIC ACID AMIDES OF ALKOXYALKYLAMINES

This is a division of application Ser. No. 738,202, filed May 24, 1985 and now U.S. Pat. No. 4,603,011.

FIELD OF THE INVENTION

This invention relates to a novel group of compounds and more particularly to a novel group of compounds particularly well suited as sweeteners in edible foodstuff.

DESCRIPTION OF THE PRIOR ART

Sweetness is one of the primary taste cravings of both animals and humans. Thus, the utilization of sweetening agents in foods in order to satisfy this sensory desire is well established.

Naturally occuring carbohydrate sweeteners such as sucrose, are still the most widely used sweetening agents. While thse naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietetic or other functional consideration.

In an attempt to eliminate the disadvantages concomitant with natural sweeteners, considerable research and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose, etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; and U.S. Pat. No. 3,717,477.

Accordingly, much work has continued in an attempt to develop and identify compounds that have a sweet taste and which will satisfy the need for better lower calorie sweeteners. Search continues for sweeteners that have intense sweetness, that is, deliver a sweet taste at low use levels and which will also produce enough sweetness at low levels to act as sole sweetener for most sweetener applications. Furthermore, the sweeteners sought must have good temporal and sensory qualities. Sweeteners with good temporal qualities produce a time-intensity sweetness response similar to natural sweeteners without lingering. Sweeteners with good sensory qualities lack undesirable off tastes and aftertaste. Furthermore, these compounds must be economical and safe to use.

In U.S. Pat. No. 3,798,204, L-aspartyl-O-t-butyl-L-serine methyl ester and L-aspartyl-O-t-amyl-L-serine methyl ester are described as sweet compounds having significant sweetness.

In U.S. Pat. No. 4,448,716 metal complex salts of dipeptide sweeteners are disclosed. In the background of this patent a generic formula is described as an attempt to represent dipeptide sweeteners disclosed in five prior patents: U.S. Pat. No. 3,475,403; U.S. Pat. No. 3,492,131; Republic of South Africa Pat. No. 695,083 published July 10, 1969; Republic of South Africa Pat. No. 695,910 published Aug. 14, 1969. The general formula attempting to represent these patents is as follows:

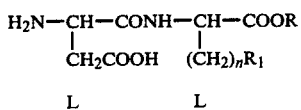

wherein R represents the lower alkyls, lower alkylaryls and cycloalkyls, n stands for integers 0 through 5, $R_1$ represents (a) phenyl group, (b) lower alkyls, (c) cycloalkyls, (d) $R_2$.

Where $R_2$ is hydroxy, lower alkoxy, lower alkyl, halogen, (e) $(S(O))_m$ (lower alkyl) where m is 0, 1 or 2 and provided n is 1 or 2, (f) $R_3$.

Where $R_3$ represents an hydroxy or alkoxy and (g) single or double unsaturated cycloalkyls with up to eight carbons. These compounds also are not entirely satisfactory in producing a high quality sweetness or in producing a sweet response at lower levels of sweetener.

Dipeptides of aspartyl-cysteine and aspartylmethionine methyl esters are disclosed by Brussel, Peer and Van der Heijden in *Chemical Senses and Flavour*, 4, 141–152 (1979) and in *Z. Lebensm. Untersuch-Forsch.*, 159, 337–343 (1975). The authors disclose the following dipeptides:

α-L-Asp-L-Cys(Me)-OMe
α-L-Asp-L-Cys(Et)-OMe
α-L-Asp-L-Cys(Pr)-OMe
α-L-Asp-L-Cys(i-Pr)-OMe
α-L-Asp-L-Cys(t-But)-OMe
α-L-Asp-L-Met-OMe

In U.S. Pat. No. 4,399,163 to Brennan et al., sweeteners having the following formulas are disclosed:

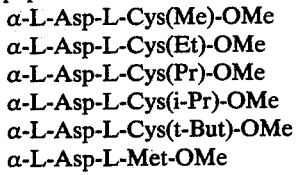

and physiologically acceptable cationic and acid addition salts thereof wherein $R^a$ is $CH_2OH$ or $CH_2OCH_3$;

R is a branched member selected from the group consisting of fenchyl, diisopropylcarbinyl, d-methyl-t-butylcarbinyl, d-ethyl-t-butyl-carbinyl, 2-methylthio-2,4-dimethylpentan-3-yl, di-t-butyl-carbinyl,

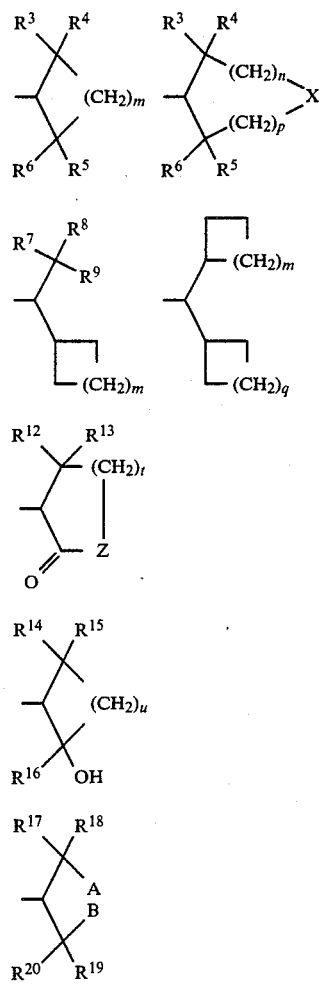

In a related patent, U.S. Pat. No. 4,411,925, Brennan, et al. disclose compounds of the above general formula with R being defined hereinabove, except $R^a$ is defined as methyl, ethyl, n-propyl or isopropyl.

U.S. Pat. No. 4,375,430 to Sklavounos discloses dipeptide sweeteners which are aromatic sulfonic acid salts of L-aspartyl-D-alaninoamides or L-aspartyl-D-serinamides.

European Patent Application No. 95772 to Tsau describe aspartyl dipeptide sweeteners of the formula:

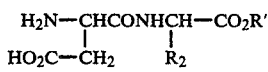

wherein R' is alkyl of 1 to 6 carbons, and $R_2$ is phenyl, phenylakylenyl or cyclohexylalkenyl, wherein the alkenyl group has 1 to 5 carbons. Closely related is U.S. Pat. No. 4,439,460 to Tsau, et al. which describes dipeptide sweeteners of the formula:

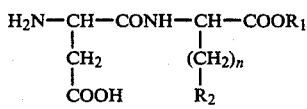

wherein n is an integer from 0 to 5, and $R_1$ is an alkyl, alkylaryl or alicyclic radical. Similar such compounds are described in many related patents, the major difference being the definition of $R_2$.

In U.S. Pat. No. 3,978,034 to Sheehan, et al., $R_2$ is defined as cycloalkenyl or phenyl. U.S. Pat. No. 3,695,898 to Hill defines $R_2$ as a mono- or a di-unsaturated alicyclic radical. Haas, et al. in U.S. Pat. No. 4,029,701 define $R_2$ as phenyl, lower alkyl or substituted or unsubstituted cycloalkyl, cycloalkenyl or cycloalkadienyl, or $S(O)_m$ lower alkyl provided that n is 1 or 2 and m is 0 or 2. Closely related are U.S. Pat. Nos. 4,448,716, 4,153,737, 4,031,258, 3,962,468, 3,714,139, 3,642,491, and 3,795,746.

U.S. Pat. No. 3,803,223 to Mazur, et al. describe dipeptide sweeteners and anti-inflammatory agents having the formula:

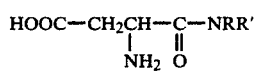

wherein R is hydrogen or a methyl radical and R' is a radical selected from the group consisting of alkyl, or

wherein Alk is a lower alkylene radical, X is hydrogen or hydroxy, and Y is a radical selected from the group consisting of cyclohexyl, naphthyl, furyl, pyridyl, indolyl, phenyl and phenoxy.

Goldkamp, et al. in U.S. Pat. No. 4,011,260 describe sweeteners of the formula:

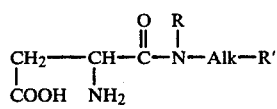

wherein R is hydrogen or a lower alkyl radical, Alk is a lower alkylene radical and R' is a carbocyclic radical. Closely related is U.S. Pat. No. 3,442,431.

U.S. Pat. No. 4,423,029 to Rizzi describes sweeteners of the formula:

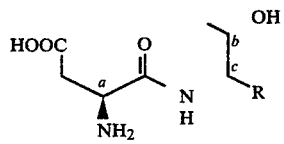

wherein R is $C_4$–$C_9$ straight, branched or cyclic alkyl, and wherein carbons a, b and c have the (S) configuration.

European Patent Application No. 48,051 describes dipeptide sweeteners of the formula:

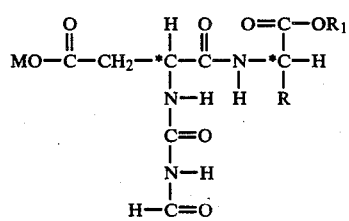

wherein

M represents hydrogen, ammonium, alkali or alkaline earth,

R represents

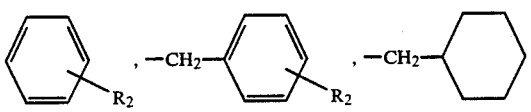

$R_1$ represents methyl, ethyl, propyl, $R_2$ represents —OH, or $OCH_3$,

* signifies an L-optical configuration for this atom.

German Patent Application No. 7259426 discloses L-aspartyl-3-fenchylalanine methyl ester as a sweetening agent.

U.S. Pat. No. 3,971,822 to Chibata, et al., disclose sweeteners having the formula:

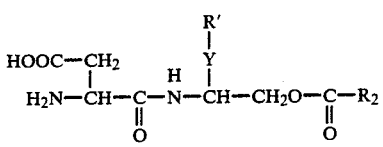

wherein R' is hydrogen or hydroxy, $R_2$ is alkyl of one to five carbon atoms, alkenyl of two to three carbon atoms, cycloalkyl of three to five carbon atoms or methyl cycloalkyl of four to six carbon atoms and Y is alkylene of one to four carbon atoms.

U.S. Pat. No. 3,907,366 to Fujino, et al. discloses L-aspartyl-aminomalonic acid alkyl fenchyl diester and its physiologically acceptable salts as useful sweeteners. U.S. Pat. No. 3,959,245 disclose the 2-methyl cyclohexyl analog of the abovementioned patent.

U.S. Pat. No. 3,920,626 discloses N-α L-aspartyl derivatives of lower alkyl esters of O-lower-alkanoyl-L-serine, β-alanine, γ-aminobutyric acid and D-β-aminobutyric acid as sweeteners.

Miyoshi, et al. in *Bulletin of Chemical Society of Japan*, 51, p. 1433–1440 (1978) disclose compounds of the following formula as sweeteners:

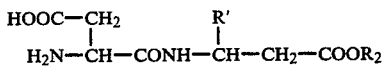

wherein R' is H, $CH_3$, $CO_2CH_3$, or benzyl and $R_2$ is lower alkyl or unsubstituted or substituted cycloalkyl.

European Patent Application No. 128,654 describes gem-diaminoalkane sweeteners of the formula:

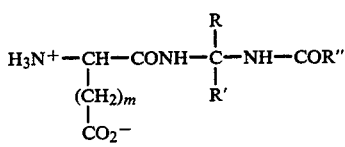

wherein m is 0 or 1, R is lower alkyl (substituted or unsubstituted), R' is H or lower alkyl, and R" is a branched alkyl, alkylcycloalkyl, cycloalkyl, polycycloalkyl, phenyl, or alkyl-substituted phenyl, and physically acceptable salts thereof.

U.S. Pat. No. 3,801,563 to Nakajima, et al. disclose sweeteners of the formula:

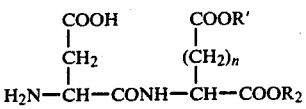

wherein R' is a branched or cyclic alkyl group of 3 to 8 carbon atoms, $R_2$ is a lower alkyl group of 1 to 2 carbon atoms and n is a integer of 0 or 1.

European Patent Application No. 34,876 describes amides of L-aspartyl-D-amino acid dipeptides of the formula:

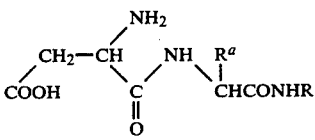

wherein $R^a$ is methyl, ethyl, n-propyl or isopropyl and R is a branched aliphatic, alicyclic or heterocyclic member which is branched at the alpha carbon atom and also branched again at one or both of the beta carbon atoms. These compounds are indicated to be of signficant sweetness.

In the *Journal of Medicinal Chemistry*, 1984, Vol. 27, No. 12, pp. 1663–8, are described various sweetener dipeptide esters, including L-aspartyl-α-aminocycloalkane methyl esters.

The various dipeptide esters of the prior art have been characterized as lacking significant stability at low pH values and/or thermal stability. These characteristics have limited the scope of use of these sweeteners in food products which are of low pH values or are prepared or served at elevated temperatures.

Accordingly, it is desired to find compounds that provide quality sweetness when added to foodstuffs or pharmaceuticals at low levels and thus eliminate or greatly diminish the aforesaid disadvantages associated with prior art sweeteners.

SUMMARY OF THE INVENTION

The present new compounds are amides of certain α-aminodicarboxylic acids and alkoxyalkylamines which are low calorie sweeteners that possess a high order of sweetness with pleasing taste and higher stability at acid pH and elevated temperatures compared to known dipeptide sweeteners.

This invention provides new sweetening compounds represented by the formula:

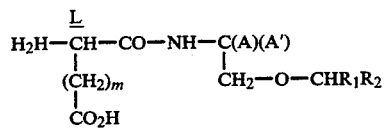

wherein,

A is H, alkyl containing 1–3 carbon atoms, hydroxyalkyl containing 1–3 carbon atoms, alkoxymethyl wherein the alkoxy group contains 1–3 carbon atoms, or $CO_2R$ in which R is alkyl containing 1–3 carbon atoms;

A' is H or $CH_3$;

A and A' when taken together with the carbon atom to which they are attached form a cycloalkyl containing 3–4 carbon atoms;

$R_1$ and $R_2$ are each a branched-chain alkyl containing 3-5 carbon atoms; and $m = 0$ or 1;

and food-acceptable salts thereof.

DESCRIPTION OF PREFERRED EMBODIMENTS

Preferred compounds include those wherein, $R_1$ and $R_2$ contain a total of 6-8 carbon atoms, especially where at least one of $R_1$ and $R_2$ is a tertiary alkyl. Of these the preferred are those wherein both $R_1$ and $R_2$ are tertiary alkyl. Particularly preferred are the compounds in which $R_1$ and $R_2$ are each tertiary butyl since these compounds, in present experience, appear to provide the highest sweetness in standard comparison determinations with sucrose.

Alkyl groups illustrative of $R_1$ and $R_2$ include isopropyl, sec-butyl, sec-amyl, tertiary butyl and tertiary amyl. Of these, tertiary butyl is preferred, as previously indicated, especially where $R_1$ and $R_2$ are each tertiary butyl.

In those compounds in which A is $CO_2R$, the preferred are those in which R is methyl. Of the substituents representative of A, the preferred are methyl, methoxymethyl and carbomethoxy in view of their high sweetness and/or stability.

Particularly preferred compounds of this invention include:

N-L-aspartyl 0-[di-(t-butyl)methyl]serine methyl ester.

N-L-aspartyl 2-amino-3-[di-(t-butyl)methoxy]propane.

N-L-aspartyl 2-amino-2-methyl-3-[di-(t-butyl)methoxy]propane.

N-L-aspartyl 2-amino-1-methoxy-3-[di-(t-butyl)methoxy]propane.

N-L-aspartyl 1-amino-1-[di-(t-butyl)methoxymethyl]-cyclopropane.

N-L-aspartyl 0-[di-(t-amyl)methyl]serine methyl ester.

N-L-aspartyl 2-amino-3-[di-(t-amyl)methoxy]propane.

N-L-aspartyl 2-amino-2-methyl-3-[di-(t-amyl)methoxy]propane.

N-L-aspartyl 2-amino-1-methoxy-3-[di-(t-amyl)methoxy]propane.

N-L-aspartyl 1-amino-1-[di-(t-amyl)methoxymethyl]-cyclopropane.

N-L-aspartyl 0-[di-(isopropyl)methyl]serine methyl ester.

N-L-aspartyl 2-amino-3-[di-(isopropyl)methoxy]propane.

N-L-aspartyl 2-amino-2-methyl-1-[di-(isopropyl)methoxy]propane.

N-L-aspartyl 1-amino-1-[di-(isopropyl)methoxy]-methyl cyclopropane.

N-L-aspartyl 2-amino-3-methoxy-1-[di-(isopropyl)-methoxy]propane.

N-L-aspartyl 2-amino-1-[di-(isopropyl)methoxy]-3-hydroxy propane.

N-L-aspartyl 2-amino-1-[di-(isopropyl)methoxy]-3-methoxy propane.

These novel compounds are effective sweetness agents when used alone or in combination with other sweeteners in an ingesta, e.g., foodstuffs or pharmaceuticals. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, thiophene saccharin, meta-aminobenzoic acid, metahydroxybenzoic acid, cyclamate, chlorosucrose, dihydrochalcone, hydrogenated glucose syrups, aspartame (L-aspartyl-L-phenylalanine methyl ester) and other dipeptides, glycyrrhizin and stevioside and the like. These sweeteners when employed with the sweetness agents of the present invention, it is believed, could produce synergistic sweetness responses.

Furthermore, when the sweetness agents of the present invention are added to ingesta, the sweetness agents may be added alone or with nontoxic carriers such as the abovementioned sweeteners or other food ingredients such as acidulants and natural and artificial gums. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds are experienced over a wide pH range, e.g. 2 to 10 preferably 3 to 7 and in buffered and unbuffered formulations.

It is desired that when the sweetness agents of this invention are employed alone or in combination with another sweetner, the sweetener or combination of sweeteners provide a sucrose equivalent in the range of from about 2 weight percent to about 40 weight percent and more preferably from about 3 weight percent to about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention several reaction schemes may be employed. In one reaction scheme compounds of the general formula II (protected α-aminodicarboxylic acid) and III (etherified hydroxy amino compound) are condensed to form compounds of the general formula IV. Subsequent removal of protecting groups A and B from compounds of general formula IV give the desired compounds of general formula I.

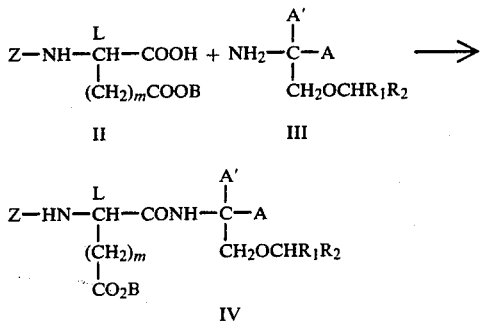

In these, group Z is an amino protecting group, B is a carboxyl protecting group and the remaining groups have the same meaning as previously described. A variety of protecting groups known in the art may be employed. Examples of many of these possible groups may be found in "Protective Groups in Organic Synthesis" by T. W. Green, John Wiley and Sons, 1981. Among the preferred groups that may be employed are benzyloxycarbonyl for Z and benzyl for B. When A includes a free hydroxy group suitable protecting groups can be employed as known in the art.

Coupling of compounds with general formula II to compounds having general formula III employs established amide-forming techniques. One such technique uses dicyclohexylcarbodiimide (DCC) as the coupling agent. The DCC method may be employed with or without additives such as 4-dimethylaminopyridine or copper(II). The DCC coupling reaction generally proceeds at room temperature, however, it may be carried out from about 31 20° to 50° C. in variety of solvents inert to the reactants. Thus suitable solvents include, but are not limited to, N,N-dimethylformamide, methylene chloride, toluene and the like. Preferably the reaction is carried out under an inert atmosphere such as argon or nitrogen. Coupling usually is complete within 2 hours but may take as long as 24 hours depending on reactants.

Various other amide-forming methods can be employed to prepare the desired compounds using suitable derivatives of the free-carboxy group in compounds of structure II, e.g., acid halide, mixed anhydride with acetic acid and similar derivatives. The following illustrates such methods using aspartic acid as the amino dicarboxylic acid.

One such method utilizes the reaction of N-protected aspartic anhydrides with the selected amino compound of formula III. Thus compounds of formula III can be reacted directly in inert organic solvents with L-aspartic anhydride having its amino group protected by a formyl, carbobenzloxy, or p-methoxycarbobenzloxy group which is subsequently removed after coupling to give compounds of general formula I. The N-acyl-L-aspartic anhydrides are prepared by reacting the corresponding acids with acetic anhydride in amounts of 1.0–1.2 moles per mole of the N-acyl-L-aspartic acid at 0° to 60° C. in an inert solvent. The N-acyl-L-aspartic anhydrides are reacted with preferably 1 to 2 moles of compounds of formula III in an organic solvent capable of dissolving both and inert to the same. Representative solvents are ethyl acetate, methyl propionate, tetrahydrofuran, dioxane, ethyl ether, N,N-dimethylformamide and benzene. The reaction proceeds smoothly at 0° to 30° C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of −10° to 50° C. and at a pH of 4–12.

Compounds of formula III are prepared by art-recognized procedures from known compounds or readily preparable intermediates. For example, the alkanol can be reacted with the appropriate nitroalkene in an inert solvent. As in any organic reaction, solvents can be employed such as methylene chloride, ether, tetrahydrofuran, dioxane, chloroform and the like. The reaction is normally effected at 0° C., but temperatures ranging from −78° C. to 100° C. can be employed. Usually an inert atmosphere of nitrogen or argon is supplied. The nitro group of the formed product is then reduced by catalytic hydrogenation, e.g., $H_2/Pd$ or $H_2$/Nickel.

Compound III can be prepared from the reaction of an alkanol and the appropriate N-protected alkyl aziridine in an inert solvent. Inert solvents include methylene chloride, ether, tetrahydrofuran, dioxane, chloroform and the like. The reaction is normally effected at cold temperatures, e.g., 0° C. but temperatures ranging from −78° C. to −100° C. can be employed. Usually an inert atmosphere of nitrogen or argon is employed.

Compounds of general formula III may be synthesized from N-protected ethanolamine compounds by employing a variety of etherification methods known in the art. Some of these methods may be found in "Modern Synthetic Reactions", 2nd ed., by H. O. House, W. A. Benjamin, Inc., 1972; "Advanced Organic Chemistry", 2nd ed., by J. March McGraw-Hill, 1977, and "Compendium of Organic Synthetic Methods", Vol. 1 and 2, by I. T. Harrison and S. Harrison, Wiley-Interscience, 1971 & 1974.

One etherification method is the base, or other catalyst, promoted reaction of N-protected ethanolamine compound with X—$CHR_1R_2$, where X is an organic leaving group such as halide, tosylate or mesylate. Any base normally employed to deprotonate an alcohol may be used, such as sodium hydride, sodium hydroxide, triethylamine, or diisopropyl ethylamine. Reaction temperatures are in the range of −78° to 100° C. and the reaction times vary from 2 to 48 hours. The reaction is carried out in a solvent that will dissolve both reactants and is inert to both as well. Solvents include, but are not limited to, diethyl ether, tetrahydrofurn, N,N-dimethylformamide, dimethylsulfoxide, and the like. Usually an inert atmosphere of nitrogen or argon is supplied.

Alternatively, a netural catalyst such as mercury (II) salts or nickel (II) 2,4-pentanedionate may be employed in this reaction. These reactions are also carried out in inert solvents at room temperature or above. The intermediate formed in this reaction is deprotected to yield compounds of formula III.

A further method of etherification is the reaction of an N-protected compound of the formula

where X is halide, tosylate, mesylate or other leaving groups, with $R_2R_1CHOH$ using a base or other catalyst. Any base normally employed to deprotonate an alcohol may be used, including sodium hydride, sodium hydroxide, triethylamine, or diisopropyl ethylamine. The reaction may be run either with or without additives, for example, copper salts. Reaction temperatures are in the range of −78° C. to 100° C., and reaction times vary from 2 to 48 hours. The reaction is carried out in a solvent that will dissolve both reactants and is inert to both. Solvents include, but are not limited to, diethyl ether, tetrahydrofuran, N,N-dimethylformamide, dimethylsulfoxide, and the like. Usually an inert atmosphere of nitorgen or argon is supplied.

Alternatively, a netural catalyst such as mercury (II) salts or nickel (II) 2,4-pentanedionate may be employed in this reaction. These are also carried out in inert solvents at room temperature or above. This product is then deprotected to yield compounds of general formula III.

The preparative procedures for formula III compounds also include a number of alternative procedures known to those skilled in the art, e.g. etherification of the corresponding hydroxyethylamine:

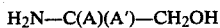

$H_2N-C(A)(A')-CH_2OH$ for example, employing a halide $X-CH(R_1)(R_2)$ preferably in the presence of a hydrogen halide acceptor, e.g. pyridine, triethylamine, and various organic amines known for this purpose.

Compounds in which A is hydroxymethyl can be prepared by reduction of the corresponding serine compound to convert the $-CO_2R$ group to $CH_2OH$ using known procedures. The $-CH_2OH$ compounds can be alkylated to form the corresponding alkoxymethyl compounds, e.g. using dimethylsulfate to form the methoxymethyl compound.

For compounds in which A and A' form a cycloalkyl group, similar procedures can be used starting with

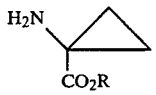

a known compound. For example, $CO_2R$ can be converted to $CH_2OH$ by reduction procedures using a variety of metal or alkylaluminum hydrides and, thereafter, the ethers formed by standard procedures.

In all cases, the amino group of formula III compounds is preferably protected in the intermediates using the usual reagents and the protecting groups removed before condensation with formula II compounds.

With regard to the removal of protecting groups from compounds of formula IV and N-protected precursors of formula III, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried at room temperature but may be conducted from 5° to 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained in the free acid form; they may also be recovered as their physiologically acceptable salts, i.e., the corresponding amino salts such as hydrochloride, sulfate, hydrosulfate, nitrate, hydrobromide, hydroiodide, phosphate or hydrophosphate; or the alkali metal salts such as the sodium, potassium, lithium, or the alkaline earth metal salts such as calcium or magnesium, as well as aluminum, zinc and like salts.

Conversion of the present new compounds of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

It is known to those skilled in the art that the compounds of the present invention having asymmetric carbon atoms may exist in racemic or optically active forms. All of these forms are contemplated within the scope of the invention.

An asymmetric carbon atom exists in those compounds where A and A' differ. Thus, optical isomers are possible in such compounds and the present compounds include such isomers. When A is $CO_2R$, i.e. the serine esters, preference exists for the L-serine compounds which appear to be sweeter than the D-compounds. In those compounds in which A is other than $CO_2R$, and A' differs from A, the same chiral configuration as in L-serine is preferred. Mixtures of the optical isomers of course, can be employed but compounds with the chiral configuration of L-serine are preferred.

The preferred isomers can be prepared by pre-selecting intermediates of appropriate configuration at the asymmetric center.

In addition to the aforesaid asymmetric center, a further such center will exist in those compounds in which $R_1$ and $R_2$ differ at the asterisked carbon atom:

$-CH(R_1)(R_2)$

The following examples further illustrate the invention:

EXAMPLE 1

N-(L-Aspartyl)-2-amino[di-(t-butyl)methoxy]propane

Di-t-butylmethanol

To a solution of trimethylacetaldehyde (5.12 g, 59.4 mmol) in anhydrous tetrahydrofuran (15 ml) at −78° C. under an argon atmosphere is added 40.9 ml of a solution of t-butyllithium in hexanes (1.6M, 65.4 mmol). The mixture is allowed to warm from −78° to room temperature over 2 hours. The reaction is quenched with 25 ml of 1M hydrochloric acid and the resulting mixture extracted with two 25 ml portions of ether. The combined ethereal extracts were washed with saturated sodium bicarbonate solution and water, dried over magnesium sulfate, and the solvent evaporated to yield a yellow oil (9.3 g) which is purified by vacuum distillation to yield a colorless oil.

Method A:

Di-t-butylmethanol is added to a dry flask under argon at 0° C. Dry tetrahydrofuran is added with a syringe. Sec-Butyl lithium (1.5M in Hexanes) is added quickly in one portion and the contents of the flask are stirred for one hour at room temperature. A 10 mM solution of 18-crown-6-ether in acetonitrile is added with a syringe and the flask cooled to 0° C. A tetrahydrofuran solution of 2-nitropropene is added with vigorous stirring over a 10 minute period. After completion of the reaction as judged by thin layer chromatography, it is quenched with saturated ammonium chloride and extracted with ethyl acetate. The organic layer is dried over $MgSO_4$ and evaporated to yield 2-nitro 1-[di-(t-butyl)methoxy]propane.

This product is dissolved in methanol and hydrogenated at 50 psi with Raney nickel T-1 as a catalyst. The reaction mixture is filtered through Celite and evaporated to yield 2-amino 1-[di-(t-butyl)methoxy]propane.

Method B:

2-Methyl aziridine is dissolved in $CH_2Cl_2$ and triethylamine under argon at 0° C. Benzylchloroformate is added and the contents of the flask are at room temperature overnight. The mixture is poured into 10% citric acid and is extracted with $CHCl_3$. The organic layer is washed with dilute aqueous $NaHCO_3$ and dried over $MgSO_4$. The solution is evaporated to yield N-Cbz-2-methyl aziridine.

N-Cbz-2-Methyl aziridine and di-t-butylmethanol are dissolved in $CH_2Cl_2$ at 0° C. under argon. Boron trifluoride etherate is added and the flask is stirred overnight. The contents are poured into saturated $NaHCO_3$ and are extracted with ethyl acetate. The organic layer is dried over $MgSO_4$ and evaporated to yield N-Cbz-2-amino 1-[di-(t-butyl)methoxy]propane.

N-Cbz-2-Amino 1-[di-(t-butyl)methoxy]propane is dissolved in $CH_3OH$ and hydrogenated over 5% Pd/C in a Paar hydrogenation apparatus. When the reaction is complete the mixture is filtered through Celite and concentrated to yield 2-amino 1-[di-(t-butyl)methoxy]propane.

To a magnetically stirred solution of 2-amino 1-[di-(t-butyl)methoxy]propane in dry dimethylformamide at 0° C. under argon atmosphere is added N-Cbz-L-aspartic acid beta-benzyl ester followed by copper (II) chloride and dicyclohexyl cabodiimide. This is stirred for 18 hours, after which the reaction mixture is poured into 0.1N HCl and extracted with ethyl acetate. The organic phase is washed with saturated $NaHCO_3$ and then water, and dried over $MgSO_4$. Evaporation of the solvent yielded N-(N'-Cbz-L-aspartyl beta-benzyl ester) 2-amino 1-[di-(t-butyl)methoxy]propane.

N-(N'-Cbz-L-aspartyl beta-benzyl ester) 2-amino-1-[di-(t-butyl)methoxy]propane is dissolved in $CH_3OH$ and hydrogenated over 5% Pd/C in a Paar apparatus. Upon completion of the reaction the mixture is filtered and concentrated to yield N-(L-aspartyl)-2-amino-1-[di-(t-butyl)methoxy]propane.

Similarly, by using the appropriate starting materials, the following compounds are also prepared:

N-(L-Aspartyl)-2-amino-1-[di-(t-amyl)methoxy]propane

N-(L-Aspartyl)-2-amino-1-[di-(isopropyl)methoxy]propane

N-(L-Aspartyl)-2-amino-1-[(isopropyl-t-butyl)methoxy]propane

EXAMPLE 2

N-(L-Aspartyl)-2-amino-2-methyl-1-[di-(t-butyl)methoxy]propane (1) Di-t-butylmethanol To a solution of trimethylacetaldehyde (5.12 g, 59.4 mmol) in anhydrous tetrahydrofuran (15 ml) at −78° C. under an argon atmosphere is added 40.9 ml of a solution of t-butyllithium in hexanes (1.6M, 65.4 mmol). The mixture is allowed to warm from −78° to room temperature over 2 hours. The reaction is quenched with 25 ml of 1M hydrochloric acic and the resulting mixture extracted with two 25 ml portions of ether. The combined ethereal extracts were washed with saturated sodium bicarbonate solution and water, dried over magnesium sulfate, and the solvent evaporated to yield a yellow oil (9.3 g) which is purified by vacuum distillation to yield a colorless oil.

(2) 2-amino-2-methyl-1-[di-(t-butyl)methoxy]propane

Method A:

Di-t-butylmethanol is added to a dry flask under argon at 0° C. Dry tetrahydrofuran is added with a syringe. Sec-Butyl lithium (1.5M in Hexanes) is added quickly in one portion and the contents of the flask are stirred for one hour at room temperature. A 10 mM solution of 18-crown-6-ether in acetonitrile is added with a syringe and the flask cooled to 0° C. A tetrahydrofuran solution of 2-nitropropene is added with vigorous stirring over a 10 minute period. After completion of the reaction, as judged by thin layer chromatography, it is quenched with dimethyl sulfate, poured into saturated ammonium chloride and extracted with ethyl acetate. The organic layer is dried over $MgSO_4$ and evaporated to yield 2-nitro-2-methyl-1-[di-(t-butyl)methoxy]propane.

This product is dissolved in methanol and hydrogenated at 50 psi with Raney nickel T-1 as a catalyst. The reaction mixture is filtered through Celite and evaporated to yield 2-amino-2-methyl-1-[di-(t-butyl)methoxy]propane.

Method B:

2,2-Dimethyl aziridine is dissolved in $CH_2Cl_2$ and triethylamine under argon at 0° C. Benzylchloroformate is added and the contents of the flask are stirred at room temperature overnight. The mixture is poured into 10% citric acid and extracted with $CHCl_3$. The organic layer is washed with dilute aqueous $NaHCO_3$ and dried over $MgSO_4$. The solution is evaporated to yield N-Cbz-2,2-dimethylaziridine.

N-Cbz-2,2-Dimethyl aziridine and di-t-butylmethanol are dissolved in $CH_2Cl_2$ at 0° C. under argon. Boron trifluoride etherate is added and the flask is stirred overnight. The contents are poured into saturated $NaHCO_3$ and extracted with ethyl acetate. The organic layer is dried over $MgSO_4$ and evaporated to yield N-Cbz-2-amino-2-methyl-1-[di-(t-butyl)methoxy]propane.

N-Cbz-2-amino-2-methyl-1-[di-(t-butyl)methoxy]propane is dissolved in $CH_3OH$ and hydrogenated over 5% Pd/C in a Paar hydrogenation apparatus. When the reaction is complete the mixture is filtered through Celite and concentrated to yield 2-amino-2-methyl-1-[di-(t-butyl)methoxy]propane.

Method C:

2-Methyl-2-amino-1-propanol is dissolved in saturated aqueous $NaHCO_3$ at room temperature. Di-tert-butyl di-carbonate is added in tert-butanol. The contents are stirred overnight and then extracted with ethyl acetate. The organic layer is dried over MgSO$_4$ and filtered. The filtrate is evaporated to give N-Boc-2-amino-2-methyl-1-propanol.

N-Boc-2-Amino-2-methyl-1-propanol is dissolved in triethylamine under argon at 0° C. Methanesulfonyl chloride is added and the mixture is stirred overnight. The solution is poured into 10% aqueous citric acid and extracted with ethyl acetate. The organic layer is dried over MgSO$_4$, filtered and evaporated to give N-Boc-2-amino-2-methyl-1-O-mesylate.

Di-t-butylmethanol is added to a dry flask under argon at 0° C. Dry tetrahydrofuran is added with a syringe. Sec-Butyl lithium (1.5M in Hexanes) is added quickly in one portion and the contents of the flask are stirred for one hour at room temperature. A 10 mM solution of 18-crown-6-ether in acetonitrile is added with a syringe and the flask cooled to 0° C. A tetrahydrofuran solution of N-Boc-2-amino-2-methyl-O-mesylate is added with vigorous stirring over a 10 minute period. After completion of the reaction, as judged by thin layer chromatography, it is quenched with dimethyl sulfate, poured into saturated ammonium chloride and extracted with ethyl acetate. The organic layer is dried over MgSO$_4$ and evaporated to yield N-Boc-2-amino-2-methyl-1-[di(t-butyl)methoxy]propane.

N-Boc-2-amino-2-methyl-1-[di-(t-butyl)methoxy]propane. propane is dissolved in trifluoroacetic acid and stirred overnight. The solution is poured into water and neutralized with 20% aqueous KOH. The mixture is extracted with ethyl acetate, dried over MgSO$_4$, filtered and evaporated to give 2-amino-2-methyl-1-[di-(t-butyl)methoxy]propane.

(3) Amide Formation

To a magnetically stirred solution of 2-amino-2-methyl-1-[di(t-butyl)methoxy]propane in dry dimethylformamide at 0° C. under argon atmosphere is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated NaHCO$_3$ and then water, and dried over MgSO$_4$. Evaporation of the solvent yields N-(N'-Cbz-L-aspartyl beta-benzyl ester)-2-amino-2-methyl-1-[di-(t-butyl)methoxy]propane.

The product of the above paragraph is dissolved in CH$_3$OH and hydrogenated over 5% Pd/C in a Paar apparatus. Upon completion of the reaction the mixture is filtered and concentrated to yield N-(L-Aspartyl)-2-amino-2-methyl-1-[di-(t-butyl)methoxy]propane.

Similarly, by using the appropriate starting materials, the following compounds are also prepared:
N-(L-Aspartyl)-2-amino-2-methyl-1-[di-(t-amyl)methoxy]propane.
N-(L-Aspartyl)-2-amino-2-methyl-1-[di-(isopropyl)methoxy]propane.
N-(L-Aspartyl)-2-amino-2-methyl-1-[(isopropyl-t-butyl)methoxy]propane.

EXAMPLE 3

N-L-Aspartyl-2-amino-1-[(di-t-butyl)methoxy]methylcyclopropane

Di-t-butylmethanol

To a solution of trimethylacetaldehyde (5.12 g, 59.4 mmol) in anhydrous tetrahydrofuran (15 ml) at −78° C. under an argon atmosphere is added 40.9 ml of a solution of t-butyllithium in hexanes (1.6M, 65.4 mmol). The mixture is allowed to warm from −78° to room temperature over 2 hours. The reaction is quenched with 25 ml of 1M hydrochloric acic and the resulting mixture extracted with two 25 ml portions of ether. The combined ethereal extracts were washed with saturated sodium bicarbonate solution and water, dried over magnesium sulfate, and the solvent evaporated to yield a yellow oil (9.3 g) which is purified by vacuum distillation to yield a colorless oil of Di-t-butylmethanol.

To a suspension of 1-amino-1-cyclopropane carboxylic acid in dry diethyl ether under argon at 0° C. is slowly added 1M borane in tetrahydrofuran with vigorous stirring. The contents are stirred overnight and then water is added dropwise to destroy the remainder of the borane. The mixture is acidified with 2N HCl and then brought to approximately pH 11 with 20% KOH and saturated with NaCl. The product is extracted with ethyl acetate and the organic layer dried over MgSO$_4$. Filtration and evaporation of the solvent yields 1-amino-1-hydroxymethylcyclopropane.

1-Amino-1-hydroxymethylcyclopropane is dissolved in saturated aqueous NaHCO$_3$ at room temperature. Di-tert-butyl dicarbonate is added in tert-butanol. The contents are stirred overnight and then extracted with ethyl acetate. The organic layer is dried over MgSO$_4$ and filtered. The filtrate is evaporated to give N-Boc-1-amino-1-hydroxymethylcyclopropane.

N-Boc-1-amino-1-hydroxymethylcyclopropane is dissolved in triethylamine under argon at 0° C. Methanesulfonyl chloride is added with a syringe and the contents stirred at room temperature overnight. The solution is poured into 10% aqueous citric acid and extracted with ethyl acetate. The organic layer is dried over MgSO$_4$, filtered and evaporated to give N-Boc-1-amino-1-hydroxymethylcyclopropane-O-mesylate.

Di-t-butylmethanol is added to a dry flask under argon at 0° C. Dry tetrahydrofuran is added with a syringe. Sec-Butyl lithium (1.5M in Hexanes) is added quickly in one portion and the contents of the flask are stirred for one hour at room temperature. A 10 mM solution of 18-crown-6-ether in acetonitrile is added with a syringe and the flask cooled to 0° C. A tetrahydrofuran solution of N-Boc-1-amino-1-hydroxymethylcyclopropane-O-mesylate is added with vigorous stirring over a 10 minute period. After completion of the reaction, as judged by thin layer chromatography, it is quenched with dimethyl sulfate, poured into saturated ammonium chloride and extracted with ethyl acetate. The organic layer is dried over MgSO$_4$ and evaporated to yield N-Boc-1-amino 1-[di-(t-butyl)methoxy]methyl cyclopropane.

The above product is dissolved in trifluoroacetic acid and stirred overnight. The solution is poured into water and neutralized with 20% aqueous KOH. The mixture is extracted with ethyl acetate, dried over MgSO$_4$, filtered and evaporated to give 1-[(di-t-butyl)methoxy-1-amino]methylcyclopropane.

To a magnetically stirred solution of 1-amino-1-[di-(t-butyl)methoxy]methylcyclopropane in dry dimethylformamide at 0° C. under argon atmosphere is added N-Cbz-L-aspartyl acid beta-benzyl ester followed by cooper (II) chloride and dicyclohexylcarbodiimide. This is stirred for 18 hours after which the reaction mixture is poured into 0.1 N HCL and extracted with ethyl acetate. The organic phase is washed with saturated NaHCO$_3$ and then water, and dried over MgSO$_4$.

Evaporation of the solvent yields N-(N'-Cbz-L-aspartyl beta-benzyl ester)-1-amino-1-[di-(t-butyl)methoxy]methylcyclopropane.

The above product is dissolved in absolute ethanol to give a 0.1M solution. An equivalent weight of 10% palladium on carbon is added and the solution is cooled in an ultra-sound ice bath. Cyclohexadiene (10 equivalents) is added and sonication is begun. After the reaction is complete as judged by thin layer chromatography, the mixture is filtered through Celite with ethanol and evaporated to yield the final product.

Similarly, by using the appropriate alkanol, the following compounds are also prepared:
N-(L-aspartyl)-1-amino-1-[di-(t-amyl)methoxy]methylcyclopropane.
N-(L-aspartyl)-1-amino-1-[di-(isopropyl)methoxy]methylcyclopropane.
N-(L-aspartyl)-1-amino-1-[(isopropyl-t-butyl)methoxy]methylcyclopropane.

EXAMPLE 4

N-(L-Aspartyl)-0-(di-t-butyl)methyl-L-serine methyl ester

A. Di-t-butylmethanol

To a solution of trimethylacetaldehyde (5.12 g, 59.4 mmol) in anhydrous tetrahydrofuran (15 ml) at −78° C. under an argon atmosphere is added 40.9 ml of a solution of t-butyllithium in hexanes (1.6M, 65.4 mmol). The mixture is allowed to warm from −78° to room temperature over 2 hours. The reaction is quenched with 25 ml of 1M hydrochloric acic and the resulting mixture extracted with two 25 ml portions of ether. The combined ethereal extracts were washed with saturated sodium bicarbonate solution and water, dried over magnesium sulfate, and the solvent evaporated to yield a yellow oil (9.3 g) which is purified by vacuum distillation to yield a colorless oil.

B. L-N-Triphenylmethyl serine methyl ester

A solution of L-serine methyl ester hydrochloride (100 g), triphenylmethylchloride (179.3 g) and triethylamine (197 ml) was stirred at 0° C. for 2 hours, then allowed to warm to room temperature overnight. The solution was diluted with diethyl ether and then washed successively with 10% aqueous citric acid and water, dried over magnesium sulfate, and the solvent evaporated to yield the product (212 g., 91%).

C. L-N-Triphenylmethyl-aziridine-2-carboxylic acid methyl ester

A mixture of compound B (212 g), methanesulfonyl chloride (45.6 ml), and pyridine (1.76 l) was stirred at 0° C., then allowed to warm slowly to room temperature overnight. Ethyl acetate (1.5 l) was added, and the resulting solution washed with 10% aqueous citric acid and water, dried over magnesium sulfate and the solvent removed. The residual oil was dissolved in tetrahydrofuran (2.5 l) and triethylamine (143 ml) was added. The mixture was heated at reflux overnight, then cooled and most of the solvent was removed under vacuum. The residual oil was dissolved in ethyl acetate (2 l) and the solution was washed successively with 10% aqueous citric acid saturated aqueous sodium bicarbonate, and water, and then dried over magnesium sulfate, after which the solvent was evaporated under vacuum. The residue was dissolved in hot methanol and the product crystallized on cooling (115 g., 57%).

D. L-N-Benzyloxycarbonylaziridine-2-carboxylic acid methyl ester

To a cold solution (0° C.) of compound C (17.0 g) and methanol (100 ml) in dichloromethane (100 ml) was added concentrated sulfuric acid (5.0 ml). The mixture was stirred at 0° C. for 10 min. Approximately half of the solvent was removed under vacuum, and the residue was dissolved in ether. This was made basic with sodium bicarbonate and extracted with dichloromethane (3×25 ml). To these combined extracts was added triethylamine (4.36 g) and the solution was cooled to 0° C. Benzyl chloroformate (7.80 g), was added, and the mixture was allowed to warm to room temperature overnight. The solution was then washed successively with 1M aqueous hydrochloric acid and saturated aqueous sodium bicarbonate, dried over magnesium sulfate, and the solvent was removed under vacuum to yield a brown oil (7.0 g). The product was purified by column chromatography on silica gel (4:1 hexanes: ethyl acetate, eluent) to yield compound D, a pale yellow oil (3.44 g., 30%).

E. N-Benzyloxycarbonyl-0-(di-t-butyl)methyl-L-serine methyl ester

To a solution of compound D (0.67 g) and di-t-butylmethanol (1.65 g) in dichloromethane (20 ml) was added boron trifluoride diethyl etherate (15 drops). The mixture is stirred at room temperature for 4 hours, then washed with water, dried over magnesium sulfate and the solvent is evaporated. The residue is purified by column chromatography (silica gel, 10:1, hexanes: ethyl acetate, eluent) to yield compound E (0.58 g).

F. O-di-t-butylmethyl-L-serine methyl ester

The product of E is dissolved in methanol in a Paar hydrogenation bottle and purged with argon. Palladium on carbon (5%) is added and hydrogenation carried out at 50 psi. After cessation of hydrogen uptake, the contents of the bottle are filtered through Celite and evaporated to give the product.

G. N-Benzyloxycarbonyl-α-L-aspartyl-β-benzylester-0-di-t-butylmethyl-L-serine methyl ester Compound F is coupled with N-benzyloxycarbonyl-L-aspartic acid-β-benzyl ester in dimethylformamide at 0° C. under argon in the presence of $CuCl_2$, and dicyclohexylcarbodiimide. The mixture is stirred at room temperature for 3 hours and then poured into water and acidified with 2N HCl (pH 5). The product is extracted with ethyl acetate and the organic phase afforded an oil which is chromatographed on silica-gel with 2:1 petroleum ether/ethyl acetate to give an oily product (370 mg).

H.

Product G is deprotected to the final product by hydrogenation (Paar) using Pd/C (5%) in methanol purged with argon. After cessation of hydrogen uptake, the reaction mixture is filtered through Celite and evaporated to provide the unprotected product. Reverse phase chromatography on $C_{18}$ silica with 50% methanolic water gave purified product (110 mg), m. 165°–167° C.

Using the foregoing procedure, the corresponding O-di-t-amylmethyl, O-diisopropylmethyl and 1-isopropyl-1-t-butylmethyl serine ethers are prepared.

The following sensory evaluations were obtained by a panel of experts using known weight percent aqueous solutions of the above compound matched to sucrose standard solutions.

| Concentration | Sucrose Equivalent | X-Sucrose |
| --- | --- | --- |
| 0.005% | 3.3% | 660 |
| 0.010% | 6.3% | 630 |
| 0.025% | 7.3% | 308 |

It was further determined by the panel of experts that the sweetener possessed excellent temporal and sensory qualities.

EXAMPLE 5

N-(L-Aspartyl)-1-(2-amino-3-hydroxypropoxy)di-t-butylmethane

Di-t-butylmethanol

To a solution of trimethylacetaldehyde (5.12 g, 59.4 mmol) in anhydrous tetrahydrofuran (15 ml) at −78° C. under an argon atmosphere is added 40.9 ml of a solution of t-butyllithium in hexanes (1.6M, 65.4 mmol). The mixture is allowed to warm from −78° to room temperature over 2 hours. The reaction is quenched with 25 ml of 1M hydrochloric acic and the resulting mixture extracted with two 25 ml portions of ether. The combined ethereal extracts were washed with saturated sodium bicarbonate solution and water, dried over magnesium sulfate, and the solvent evaporated to yield a yellow oil (9.3 g) which is purified by vacuum distillation to yield a colorless oil.

The product of Example 4 is dissolved in ether and is reduced with LiAlH$_4$ to give -(2-amino-3-hydroxypropoxy)di-t-butylmethane. To a magnetically stirred solution of this product in dry dimethyl formamide at 0° C. under argon atmosphere is added N-Cbz-L-aspartic acid beta-benzyl ester, followed by copper (II) chloride and dicyclohexylcarbodiimide. This is stirred for 18 hours, after which the reaction mixture is poured into 0.1N HCl and extracted with ethyl acetate. The organic phase is washed with saturated NaHCO$_3$ and then water and is dried over MgSO$_4$. The solvents evaporated off to give N-(N'-Cbz-L-aspartyl beta-benzyl ester)-1-(2-amino-3-hydroxypropoxy)-di-t-butylmethane.

This product is dissolved in CH$_3$OH and hydrogenated over 5% Pd/C in a Paar apparatus. Upon completion of the reaction, the mixture is filtered and concentrated to yield the final product.

Similarly, by utilizing the above procedure, and the appropriate alkanol, the corresponding di-t-amylmethane, diisopropylmethane and 1-isopropyl-1-t-butylmethane compounds are prepared.

N-(L-Aspartyl)-1-(2-amino-3-methoxypropoxy)di-t-butylmethane

Di-t-butylmethanol

To a solution of trimethylacetaldehyde (5.12 g, 59.4 mmol) in anhydrous tetrahydrofuran (15 ml) at −78° C. under an argon atmosphere is added 40.9 ml of a solution of t-butyllithium in hexanes (1.6M, 65.4 mmol). The mixture is allowed to warm from −78° to room temperature over 2 hours. The reaction is quenched with 25 ml of 1M hydrochloric acid and the resulting mixture extracted with two 25 ml portions of ether. The combined ethereal extracts were washed with saturated sodium bicarbonate solution and water, dried over magnesium sulfate, and the solvent evaporated to yield a yellow oil (9.3 g) which is purified by vacuum distillation to yield a colorless oil.

To a suspension of N-Benzyloxycarbonyl-0-di-t-butylmethyl-L-serine methyl ester (prepared as in Example 4) in dry diethyl ether under argon at 0° C. is slowly added 1M borane in tetrahydrofuran with vigorous stirring. The contents are stirred overnight and then water is added dropwise to destroy the remainder of the borane. The mixture is acidified with 2N HCl and then brought to approximately pH 11 with 20% KOH and saturated with NaCl. The product is extracted with ethyl acetate and the organic layer dried over MgSO$_4$ and filtered and the solvent is evaporated off.

The product of the preceding paragraph is dissolved in methylene chloride and methylated with dimethylsulfate to afford the 1-(2-N-Boc-amino-3-methoxypropoxy)-di-t-butylmethane. This product is dissolved in methanol in a Paar hydrogenation bottle and purged with argon. Palladium on carbon (5%) is added and hydrogenation carried out at 50 psi. After cessation of hydrogen uptake, the contents of the bottle are filtered through celite and evaporated to give 1-(2-amino-3-methoxypropoxy)di-t-butylmethane.

To a magnetically stirred solution of this product in dry dimethyl formamide at 0° C. under argon atmosphere is added N-CbZ-L-aspartic acid beta-benzyl ester followed by copper (II) chloride and dicyclohexyl carbodiimide. This is stirred for 18 hours, after which the reaction mixture is poured into 0.1N HCl and extracted with ethyl acetate. The organic phase is washed with saturated NaHCO$_3$, and then water and dried over the MgSO$_4$. The solvent is evaporated off to give N-(N-CbZ-L-aspartyl-beta benzyl ester)-1-(2-amino-3-methoxypropoxy)di-t-butylmethane.

This product is dissolved in CH$_3$OH and hydrogenated over 5% Pd/C in a Parr apparatus. Upon completion of the reaction, the mixture is filtered and concentrated to yield the final product.

Similarly, by utilizing the above procedure and the appropriate cycloalkanol, the corresponding di-t-amylmethane, diisopropylmethane and 1-isopropyl-1-t-butylmethane compounds are prepared.

What is claimed is:

1. A compound represented by the formula:

$$\begin{array}{ccc} & \text{L} & \\ \text{H}_2\text{H}-\text{CH}-\text{CO}-\text{NH}-&\text{C}(\text{A})(\text{A}') \\ | & & | \\ (\text{CH}_2)_m & & \text{CH}_2-\text{O}-\text{CHR}_1\text{R}_2 \\ | & & \\ \text{CO}_2\text{H} & & \end{array}$$

wherein,

A is H, alkyl containing 1–3 carbon atoms, hydroxyalkyl containing 1–3 carbon atoms, or alkoxymethyl wherein the alkoxy group contains 1–3 carbon atoms;

A' is H or CH$_3$;

A and A' when taken together with the carbon atom to which they are attached form a cycloalkyl containing 3–4 carbon atoms;

R$_1$ and R$_2$ are each a branched-chain alkyl containing 3–5 carbon atoms; and m=0 or 1;

and food-acceptable salts thereof.

2. A compound according to claim 1 wherein at least one of R$_1$ and R$_2$ is a tertiary alkyl.

3. A compound according to claim 1 wherein $R_1$ and $R_2$ are each tertiary alkyl.

4. A compound according to claim 1 wherein $R_1$ and $R_2$ contain a total of 6-8 carbon atoms.

5. A compound according to claim 1 wherein $R_1$ and $R_2$ contain a total of 8 carbon atoms.

6. A compound represented by the formula:

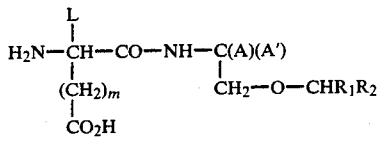

wherein
  A is H, alkyl containing 1-3 carbon atoms, or alkoxymethyl wherein the alkoxy group contains 1-3 carbon atoms;
  A' is H or $CH_3$;
  A and A' when taken together with the carbon atom to which they are attached form a cycloalkyl containing 3-4 carbon atoms;
  $R_1$ and $R_2$ are each a branched-chain alkyl containing 3-5 carbon atoms; and
  m=0 or 1;
  and food-acceptable salts thereof.

7. A compound according to claim 6 wherein at least one of $R_1$ and $R_2$ is a tertiary alkyl.

8. A compound according to claim 6 wherein $R_1$ and $R_2$ are each tertiary alkyl.

9. A compound according to claim 6 wherein $R_1$ and $R_2$ contain a total of 6-8 carbon atoms.

10. A compound according to claim 6 wherein $R_1$ and $R_2$ contain a total of 8 carbon atoms.

11. A compound represented by the formula:

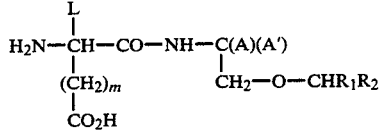

wherein
  A is alkyl containing 1-3 carbon atoms;
  A' is H or $CH_3$;
  $R_1$ and $R_2$ are each a branched-chain alkyl containing 3-5 carbon atoms; and
  m=0 or 1;
  and food-acceptable salts thereof.

12. A compound according to claim 11 wherein at least one of $R_1$ and $R_2$ is a tertiary alkyl.

13. A compound according to claim 11 wherein $R_1$ and $R_2$ are each tertiary alkyl.

14. A compound according to claim 11 wherein $R_1$ and $R_2$ contain a total of 6-8 carbon atoms.

15. A compound according to claim 11 wherein $R_1$ and $R_2$ contain a total of 8 carbon atoms.

16. A compound represented by the formula:

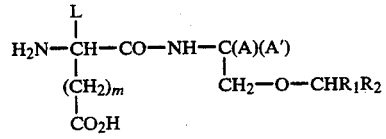

wherein
  A is alkoxymethyl wherein the alkoxy group contains 1-3 carbon atoms
  A' is H or $CH_3$;
  $R_1$ and $R_2$ are each a branched-chain alkyl containing 3-5 carbon atoms; and
  m=0 or 1;
  and food-acceptable salts thereof.

17. A compound according to claim 16 wherein at least one of $R_1$ and $R_2$ is a tertiary alkyl.

18. A compound according to claim 16 wherein $R_1$ and $R_2$ are each tertiary alkyl.

19. A compound according to claim 16 wherein $R_1$ and $R_2$ contain a total of 6-8 carbon atoms.

20. A compound according to claim 16 wherein $R_1$ and $R_2$ contain a total of 8 carbon atoms.

21. A compound represented by the formula:

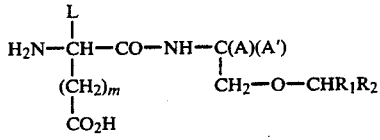

wherein
  A and A' when taken together with the carbon atom to which they are attached form a cycloalkyl containing 3-4 carbon atoms;
  $R_1$ and $R_2$ are each branched-chain alkyl containing 3-5 carbon atoms; and
  m=0 or 1;
  and food-acceptable salts thereof.

22. A compound according to claim 21 wherein at least one of $R_1$ and $R_2$ is a tertiary alkyl.

23. A compound according to claim 21 wherein $R_1$ and $R_2$ are each tertiary alkyl.

24. A compound according to claim 21 wherein $R_1$ and $R_2$ contain a total of 6-8 carbon atoms.

25. A compound according to claim 21 wherein $R_1$ and $R_2$ contain a total of 8 carbon atoms.

26. The compound according to claim 6 which is N-L-aspartyl 2-amino-3-[di-(t-butyl)methoxy]propane.

27. The compound according to claim 6 which is N-L-aspartyl 2-amino-2-methyl-3-[di-(t-butyl)methoxy]propane.

28. The compound according to claim 6 which is N-L-aspartyl 2-amino-1-methoxy-3-[di-(t-butyl)methoxy]propane.

29. The compound according to claim 6 which is N-L-aspartyl 2-amino-3-[di-(t-butyl)methoxy]propane.

30. The compound according to claim 6 which is N-L-aspartyl 1-amino-1-[di-(t-butyl)methoxy]methylcyclopropane.

31. The compound according to claim 6 which is N-L-aspartyl 2-amino-3-[di-(t-amyl)methoxy]propane.

32. The compound according to claim 6 which is N-L-aspartyl 2-amino-2-methyl-3-[di-(t-amyl)methoxy]propane.

33. The compound according to claim 6 which is N-L-aspartyl 2-amino-1-methoxy-3-[di-(t-amyl)methoxy]propane.

34. The compound according to claim 6 which is N-L-aspartyl 2-amino-3-[di(t-amyl)methoxy]propane.

35. The compound according to claim 6 which is N-L-aspartyl 1-amino-1-[di(t-amyl)methoxymethyl]cyclopropane.

* * * * *